US008802026B2

(12) United States Patent
Fulton et al.

(10) Patent No.: US 8,802,026 B2
(45) Date of Patent: Aug. 12, 2014

(54) IMMUNOASSAY ASSEMBLY AND METHODS OF USE

(75) Inventors: Scott P. Fulton, Middleton, WI (US); Robert J. Sakowski, Barneveld, WI (US); William Bowers, Topsfield, MA (US)

(73) Assignee: Agilent Technologies, Inc., Santa Clara, CA (US)

( * ) Notice: Subject to any disclaimer, the term of this patent is extended or adjusted under 35 U.S.C. 154(b) by 314 days.

(21) Appl. No.: 12/859,538

(22) Filed: Aug. 19, 2010

(65) Prior Publication Data

US 2010/0323372 A1 Dec. 23, 2010

Related U.S. Application Data

(62) Division of application No. 11/188,535, filed on Jul. 25, 2005, now Pat. No. 7,799,279.

(60) Provisional application No. 60/590,673, filed on Jul. 23, 2004.

(51) Int. Cl.
*B01L 3/00* (2006.01)

(52) U.S. Cl.
USPC ........... 422/501; 422/500; 422/504; 422/505; 422/511; 422/50; 422/400; 422/401; 422/419; 422/412; 422/402; 436/518; 436/177

(58) Field of Classification Search
USPC .................... 422/50, 400, 401, 419, 402, 412
See application file for complete search history.

(56) References Cited

U.S. PATENT DOCUMENTS

| 4,039,652 | A |   | 8/1977  | Adams et al.              |
|-----------|---|---|---------|---------------------------|
| 4,341,635 | A |   | 7/1982  | Golias                    |
| 4,452,899 | A | * | 6/1984  | Alston ............... 436/46 |
| 4,708,932 | A |   | 11/1987 | Axen et al.               |
| 4,775,635 | A |   | 10/1988 | Ebersole et al.           |
| 4,787,971 | A |   | 11/1988 | Donald                    |
| 4,797,260 | A |   | 1/1989  | Parker                    |
| 4,806,313 | A | * | 2/1989  | Ebersole et al. ....... 422/400 |
| 4,956,298 | A |   | 9/1990  | Diekmann                  |
| 5,108,704 | A |   | 4/1992  | Bowers et al.             |
| 5,336,412 | A |   | 8/1994  | Huse et al.               |
| 5,395,521 | A |   | 3/1995  | Jagadeeswaran             |
| 5,419,874 | A |   | 5/1995  | Coassin et al.            |

(Continued)

FOREIGN PATENT DOCUMENTS

| DE | 3717211    | 12/1998 |
|----|------------|---------|
| EP | 0588564    | 3/1994  |
| WO | 2004/007081 | 1/2004  |

OTHER PUBLICATIONS

HP1050 Series Pumping Systems User's Guide, Hewlett Packard, pp. 1/1-3/16, 1992.*

*Primary Examiner* — Melanie Y Brown

(57) ABSTRACT

The present invention relates to an improved system for efficiently and accurately performing immunoassays, such as ELISAs. The invention provides an immunoassay assembly which includes a flow-through unit and an aspiration pump. The immunoassay flow-through unit includes an outer seal; at least one bed support; an inner seal; and a packed non-porous bed. The unit is releasably attached to an aspiration pump which enables the controlled flow rate of liquid passing through the packed bed of the flow-through unit. The invention also provides a method of using the immunoassay assembly to identify analytical targets of interest.

2 Claims, 12 Drawing Sheets

(56) References Cited

U.S. PATENT DOCUMENTS

| | | |
|---|---|---|
| 5,437,979 A | 8/1995 | Rampal et al. |
| 5,441,645 A | 8/1995 | Sanford et al. |
| 5,496,473 A | 3/1996 | Chow |
| 5,589,063 A | 12/1996 | Sanford et al. |
| 5,610,077 A | 3/1997 | Davis et al. |
| 5,833,927 A | 11/1998 | Raybuck et al. |
| 5,861,125 A | 1/1999 | Shively |
| 5,876,918 A | 3/1999 | Wainwright et al. |
| 6,103,195 A | 8/2000 | Shukla et al. |
| 6,120,734 A | 9/2000 | Lackie |
| 6,143,252 A | 11/2000 | Haxo, Jr. et al. |
| 6,416,716 B1 | 7/2002 | Shukla et al. |
| 6,426,230 B1 | 7/2002 | Feistel |
| 6,427,731 B1 | 8/2002 | Horn |
| 6,537,502 B1 | 3/2003 | Shukla et al. |
| 6,550,349 B1 | 4/2003 | Godin |
| 6,566,145 B2 * | 5/2003 | Brewer ......................... 436/178 |
| 6,635,201 B1 | 10/2003 | Kopaciewicz et al. |
| 6,692,703 B2 | 2/2004 | Shoji et al. |
| 6,761,855 B1 | 7/2004 | Cook et al. |
| 6,770,246 B1 | 8/2004 | Husek |
| 6,911,312 B2 | 6/2005 | Anderson et al. |
| 2002/0094566 A1 | 7/2002 | Tubbs et al. |
| 2002/0110495 A1 | 8/2002 | Hunt et al. |
| 2002/0146840 A1 | 10/2002 | Hage et al. |
| 2002/0182114 A1 | 12/2002 | Ingenhoven et al. |
| 2003/0133843 A1 | 7/2003 | Hilhorst et al. |
| 2003/0178370 A1 | 9/2003 | Fisk et al. |
| 2003/0223912 A1 | 12/2003 | Knecht et al. |
| 2004/0072375 A1 | 4/2004 | Gjerde et al. |
| 2004/0122222 A1 | 6/2004 | Sakurai et al. |
| 2004/0142488 A1 | 7/2004 | Gierde et al. |
| 2005/0016921 A1 | 1/2005 | Gjerde et al. |
| 2005/0019941 A1 * | 1/2005 | Gierde et al. ................ 436/161 |
| 2005/0019950 A1 | 1/2005 | Gierde et al. |
| 2005/0019951 A1 | 1/2005 | Gjerde et al. |
| 2005/0045543 A1 | 3/2005 | Gjerde et al. |
| 2005/0255604 A1 | 11/2005 | Gjerde et al. |
| 2005/0258097 A1 | 11/2005 | Gjerde et al. |

* cited by examiner

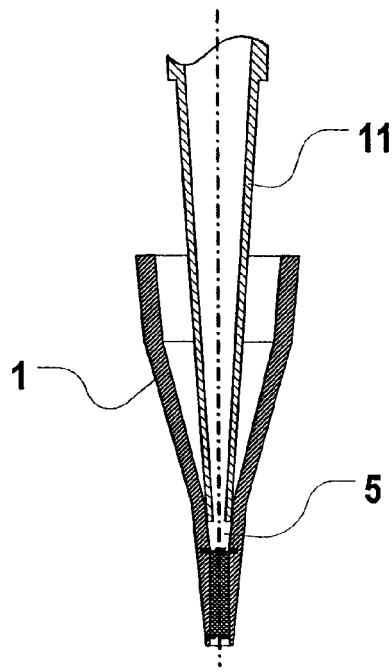
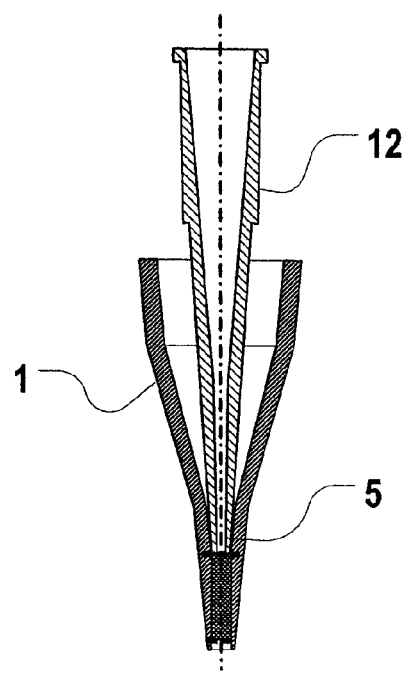
Fig. 2        Fig. 3
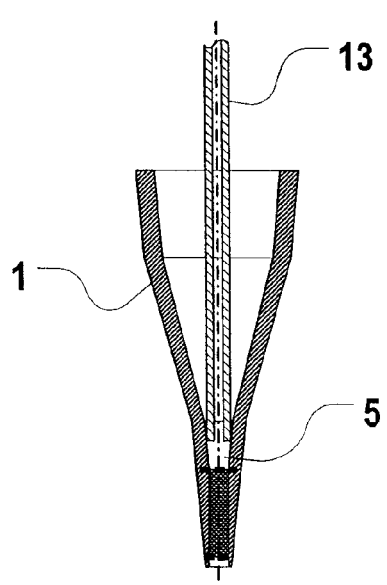
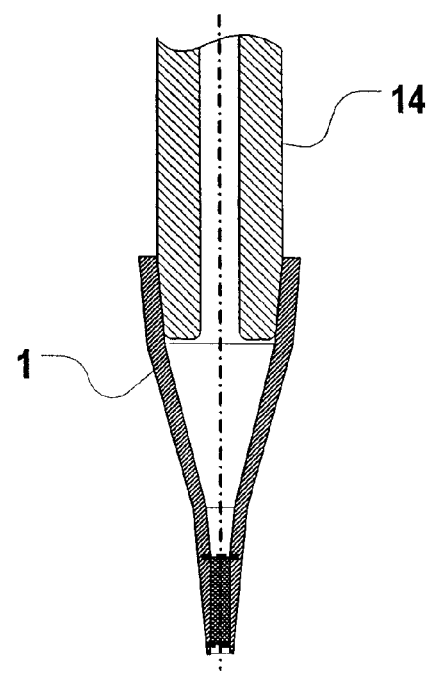
Fig. 4        Fig. 5

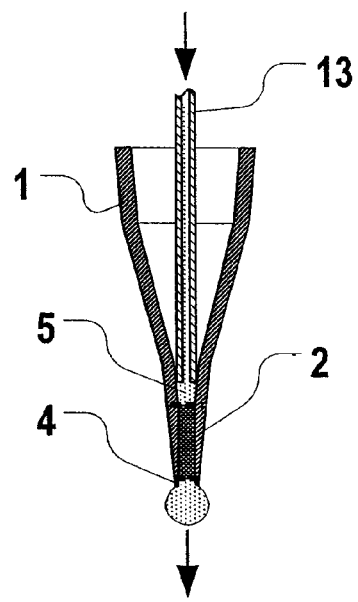 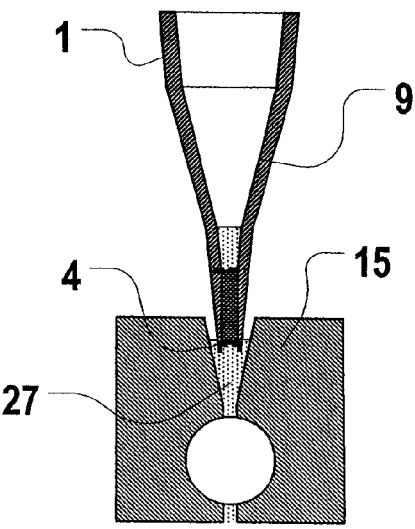
Fig. 15  Fig. 16
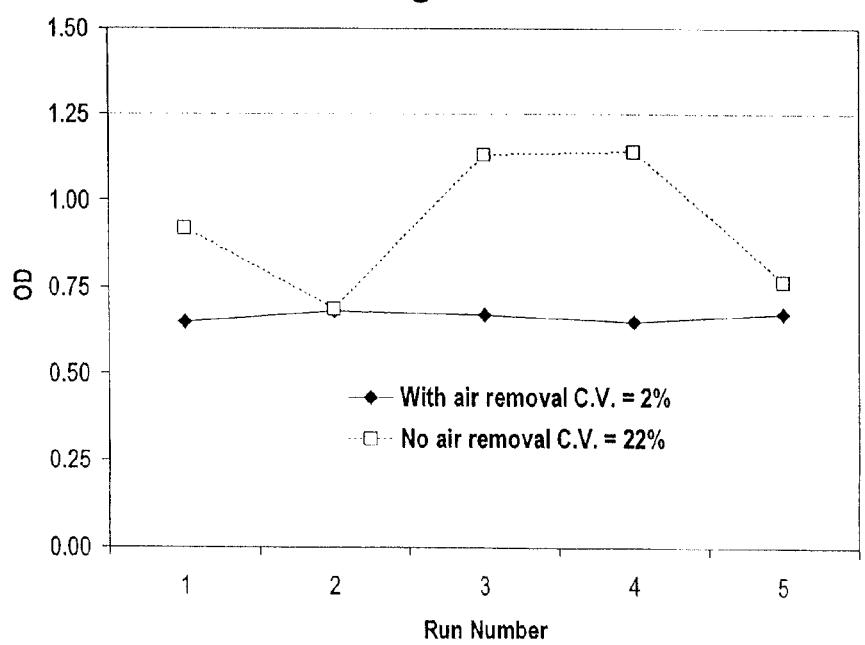
Fig. 17

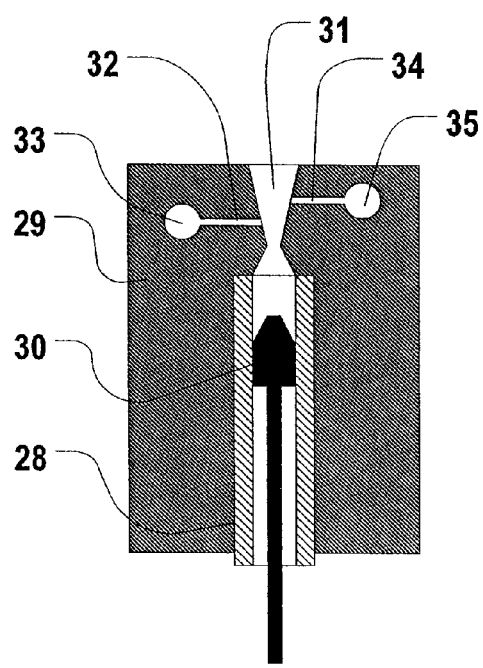
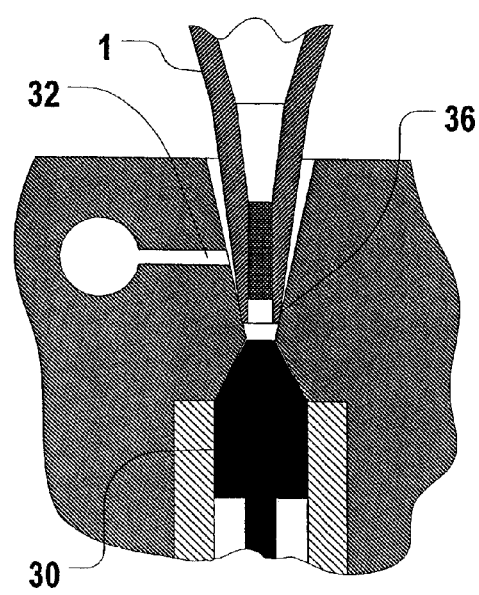
Fig. 18                      Fig. 19

IMMUNOASSAY ASSEMBLY AND METHODS OF USE

CROSS-REFERENCE TO RELATED APPLICATIONS

This is a divisional of application Ser. No. 11/188,535, filed Jul. 25, 2005, now U.S. Pat. No. 7,799,279 which claims priority to provisional application Ser. No. 60/590,673, filed Jul. 23, 2004, both of which are incorporated herein by reference.

STATEMENT REGARDING FEDERALLY SPONSORED RESEARCH OR DEVELOPMENT

None.

BACKGROUND OF THE INVENTION

The fields of life science research and pharmaceutical development are critically dependent upon highly selective and sensitive quantitative assays for a wide range of different biomolecules (such as proteins, antibodies, cytokines, receptors, enzymes, peptides, nucleic acids, hormones, and the like) in complex clinical or biological samples (such as blood, urine, tissue or cellular extracts, cell culture supernatants, bioprocess feedstreams, and the like). In typical samples (which may contain thousands of different molecular species) the analytes of interest may be present at extremely low concentrations (nanograms per milliliter or less), but the samples may be available only in very small quantities (microliters or less). The rapid growth in the field of biotechnology and the introduction of many potential new drug targets from genomic research have created an increasing demand for more rapid and efficient analytical methods, without any sacrifice in performance.

In order to simultaneously obtain high selectivity (the ability to measure one very specific molecule in a complex mixture) and high sensitivity (the ability to accurately quantify very small concentrations or amounts), a number of analytical methods have been developed which couple powerful molecular separations with extremely responsive detection methods.

One of the most widely used of these separation-based methods is the Enzyme-Linked Immuno-Sorbent Assay or ELISA. In ELISA, an antibody is immobilized on a solid phase support and exposed to a liquid sample, enabling any antigen (analytical target) to bind specifically to the antibody. Non-binding molecules in the sample are washed away. The solid phase with bound target can then be exposed to either antigen or a second antibody specific to the target that are labeled with a linked enzyme. After the non-binding labeled molecules are washed away, the solid phase is then exposed to enzyme substrate under controlled conditions so that the amount of colored or fluorescent enzyme product formed is proportional to the amount of label present, which can be used in turn to quantify the amount of target present in the original sample.

Currently in the fields of life science research and pharmaceutical development, ELISAs are done almost entirely using plastic (typically polystyrene) multi-well plates called microtiter plates or microplates. The wall of each well serves as both the solid phase for binding the antibody and antigen, as well as the container for the sample and reagents that are added. Liquid addition is done by pipetting, and washing is done by rapidly pipetting a wash solution in and out of the well. Readout of the enzyme product is done through the transparent plastic wells with an optical plate reader that measures either absorbance or fluorescence. This technique is quite simple, requires minimal specialized equipment and is very flexible in terms of the reagent systems and assay formats that can be used.

However, the microplate ELISA method suffers from a number of serious drawbacks. The most important is that the antibody is bound to the wall of the well, and thus the only way sample and reagent molecules can reach the surface to interact is by molecular diffusion. Diffusion is a relatively slow process over the potential path length of several millimeters found in a typical, microplate well, and so after liquids are added for each step, the user must allow the plate to incubate for anywhere from 30 minutes to several hours to overnight to allow the binding reaction to approach equilibrium. This makes the total assay turnaround time quite long, typically on the order of 4 to 24 hours.

In addition, microplate ELISAs are subject to a high degree of variability, due to the critical techniques required. The pipetting must be done very accurately and consistently into each well, and timing between wells can be very important. Temperature variation between the inner and outer wells in a plate can lead to variability, as can jarring or vibration of the plates during incubation. Most operators are not as careful as required due to the tedium of the work, and assay coefficients of variation of 10 to 30% or more are not uncommon. Automation of microplate ELISAs using conventional liquid handling robotic equipment is possible, but is quite complex and often does not improve reproducibility. Users often find that such automated assays must be constantly monitored by a human operator to prevent problems.

A related set of highly selective separations are used in a micro-preparative mode to isolate the target from a complex sample in preparation for mass spectroscopy (MS), using either an ElectroSpray Interface (ESI) or Matrix Assisted Laser Desorption Interface (MALDI) to ionize the sample upon entry into the instrument. MS is unique in its ability to very rapidly provide comprehensive identity and structural information on analyte molecules with high sensitivity from very small volumes of sample. Because of the rich structural information MS gives about individual molecular species (especially proteins), complex samples must be fractionated or at least significantly simplified to enable a meaningful MS analysis to be performed. Purification methods are also needed when the target of interest is present in very small concentrations relative to other components in the sample, as is often the case in clinical or biological samples. Once the samples are separated into individual fractions or peaks, additional processing (such as concentration, desalting, enzymatic digestion and/or matrix addition) often must be performed to prepare the sample for analysis by the MS instrument.

In sample prep for MS, the target molecules are selectively bound to a surface by immobilized antibodies or other selective surface groups (such as ion exchange, reversed phase, hydrophobic interaction, affinity, and the like), and non-binding contaminants are washed away. Then the bound target is eluted (using for example salt, acid or organic solvent) for collection into a tube or on a surface spot for further analytical processing. It is also possible to immobilize an enzyme (such as a protease or glycosidase) to the packed bed to enable very rapid processing of the target molecule prior to further analysis. The amounts of target analyte required for MS are very similar to those required for detection using an ELISA.

Currently two separation methods are most often used as a front-end for MS and for two-dimensional gel electrophoresis and for gradient high performance liquid chromatography (HPLC). Both of these techniques are powerful and work reasonably well for comprehensively searching through all of the components in complex samples. However, these methods are not without problems. Two-dimensional gels, for example are labor-intensive, have many steps, and require many hours or even days to complete (compared to the analysis time of the MS, which is usually a matter of seconds). HPLC is sometimes not compatible with large proteins, and instrumentation systems with comparable throughput can be almost as expensive and complex as the MS itself. Sample carryover can also be an issue in high throughput applications.

Many different types of small-scale adsorption-based separation devices have been developed, and some are offered for use in MS sample preparation. Most have been adapted from devices designed for solid phase extraction (SPE) used in general analytical chemistry. One popular approach is the "spin column", in which a small packed bed is suspended in a microcentrifuge tube, with samples and eluents driven through using a laboratory centrifuge. Some spin columns are also designed to be driven by a vacuum manifold. Spin columns are offered by a number of vendors in a range of common surface chemistries (reversed phase, ion exchange, metal chelate affinity). Although they are simple, spin columns suffer from the need to collect the final product in a test tube, then transfer it by pipette to the next step in the process or to the MS interface. These sample transfer steps can lead to significant losses, especially with dilute samples. Spin columns are poorly suited for automation. Also, most of the available spin columns are too large (typical bed volumes of 10 to 200 μL) for handling sample volumes in the low microliter range or below. It is also virtually impossible to control the flow rate through a spin column with any precision, which can reduce capture efficiency and reproducibility.

Perhaps the most popular approach to simplified sample preparation for MS is the use of modified pipette tips containing adsorbent materials. In the Millipore ZipTip product, a standard chromatographic adsorbent is embedded in a sponge-like polymer matrix in the end of the tip. The matrix enables flow by aspiration in a standard pipettor with little pressure drop. The company has also made this technology available in a 96-well plate format (ZipPlate) driven by a vacuum manifold, primarily for use in in-gel digestion and purification of 2D gel spots. Glygen has developed a tip with a flattened area at the end with the adsorbent particles embedded thermally on the inner surface, which can handle sample volumes as low as 1 to 10 μL. PhyNexus produces pipette tips containing affinity chromatography resins sandwiched between sealed-on screens in standard 200 and 1000 μL pipette tips. The tips produce final product in an elution volume of 10 to 15 μL. These pipette tip products are simple and convenient, but suffer from a number of drawbacks. If used with syringes or pipettors, it is very difficult to achieve sufficiently slow flow rates for complete binding, especially when affinity or antibody separations are used. As a result, multiple aspirate/dispense cycles are needed. This, in turn, leads to non-quantitative and/or non-reproducible capture of the bound target providing typical recoveries for proteins only in the 20 to 40% range. Like spin columns, pipette tips can only perform one separation step at a time, with some type of transfer operation required between steps, with likely concomitant sample loss. Flow through the pipette tip can only go in and out through the distal port, which limits the flexibility of operation.

A number of academic labs and companies have worked to integrate the separation and other processing steps or improve MS sensitivity through modifications to the MALDI plate itself. One example is the SELDI (Surface-Enhanced Laser Desorption Ionization) ProteinChip product from Ciphergen Biosystems. In this approach, various surface chemistries are incorporated into a spot on the plate to effect physical adsorption, ion exchange, or separations with affinity binding using antibodies or receptors, etc.). A small volume of sample is incubated on the spot, the non-binding materials washed off, and then matrix is added prior to analysis. The MALDI plate approaches are, of course, not amenable for use in electrospray MS. They are also limited to use with a single binding selectivity, so that other separation and preparation steps must be carried out elsewhere. The amount of sample that can be processed in this manner is also limited, so significant concentration is difficult to achieve.

A combined system approach has been developed by Intrinsic Bioprobes. The Mass Spectrometric ImmunoAssay (MSIA) technology developed by this company uses pipette tips incorporating a porous glass frit, onto which antibodies are immobilized. The bound antigens isolated from samples are eluted onto a MALDI plate for analysis. In other products, a pipette tip antibody-based separation device (using a porous glass monolith solid phase) is used in combination with enzymes (such as trypsin) immobilized on the MALDI plate. Gyros AB has developed a microfluidic system in the form of a compact disk (CD)-shaped device that incorporates several separation steps (including antibody affinity) driven by centrifugal force. The major application for this system are ELISA and sample preparation prior to MALDI MS. Bruker Daltonics has introduced the ClinProt system for purification prior to MALDI MS based upon robotic liquid handling and magnetic beads. Other integrated systems have some interesting advantages, but most of them require complex and expensive dedicated instrumentation for implementation.

Thus the field of biomolecule separation is one in which there is still room for improvement to overcome some of the limitations in prior art approaches and standard equipment. In particular, the use of the microtiter plate is less appropriate today given the sensitivity and speed desired by modern analytical biochemistry.

BRIEF SUMMARY OF THE INVENTION

The present invention is summarized as a novel system for efficiently and accurately performing immunoassays, such as ELISAs. One aspect of the invention provides an immunoassay assembly including a flow-through unit and an aspiration pump.

In another aspect, the invention provides a flow-through unit having an inner seal; a pair of bed supports; and a packed particle bed.

In another aspect, the flow-through unit of the invention is releasably attached to a liquid handling device.

In yet another aspect the invention also provides a method of using the immunoassay assembly to identify an analytical target, by loading a sample solution and a reagent onto a packed bed of the flow-through unit; aspirating unbound antigen and reagents such as enzyme conjugates through the unit; and identifying the analytical target of interest.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. Other objects, advantages and features of the present invention will become apparent from the following specification taken in conjunction with the accompanying drawings.

BRIEF DESCRIPTION OF THE SEVERAL VIEWS OF THE DRAWINGS

FIG. 2 is a cross-sectional view of the assay unit of FIG. 1 with a standard 200 µl pipette tip inserted therein.

FIG. 3 is a cross-sectional view similar to FIG. 2 with a standard 10 µl pipette tip inserted into the assay unit.

FIG. 4 is a cross-sectional view of an assay unit with a standard 20 gauge hypodermic needle inserted into it.

FIG. 5 is a cross-sectional view of the assay unit of FIG. 1 with a standard laboratory pipette holder inserted therein.

FIG. 15 is a cross-sectional view showing the assay unit with a needle inserted into its input shown pumping buffer through the unit to displace any air.

FIG. 16 is a cross-sectional view showing the assay unit partially filled with liquid being inserted into a partially liquid-filled input to the aspiration pump.

FIG. 17 is a graphical representation of data showing absorbance (OD) signals of repeats of the same sample for a direct ELISA assay with and without air entrapped in the assay unit.

FIG. 18 is a cross-sectional view through an aspiration or piston pump constructed in accordance with another aspect of the present invention.

FIG. 19 is an enlarged cross-sectional view showing an assay unit inserted into the pump of FIG. 18.

DETAILED DESCRIPTION OF THE INVENTION

Figure 1:
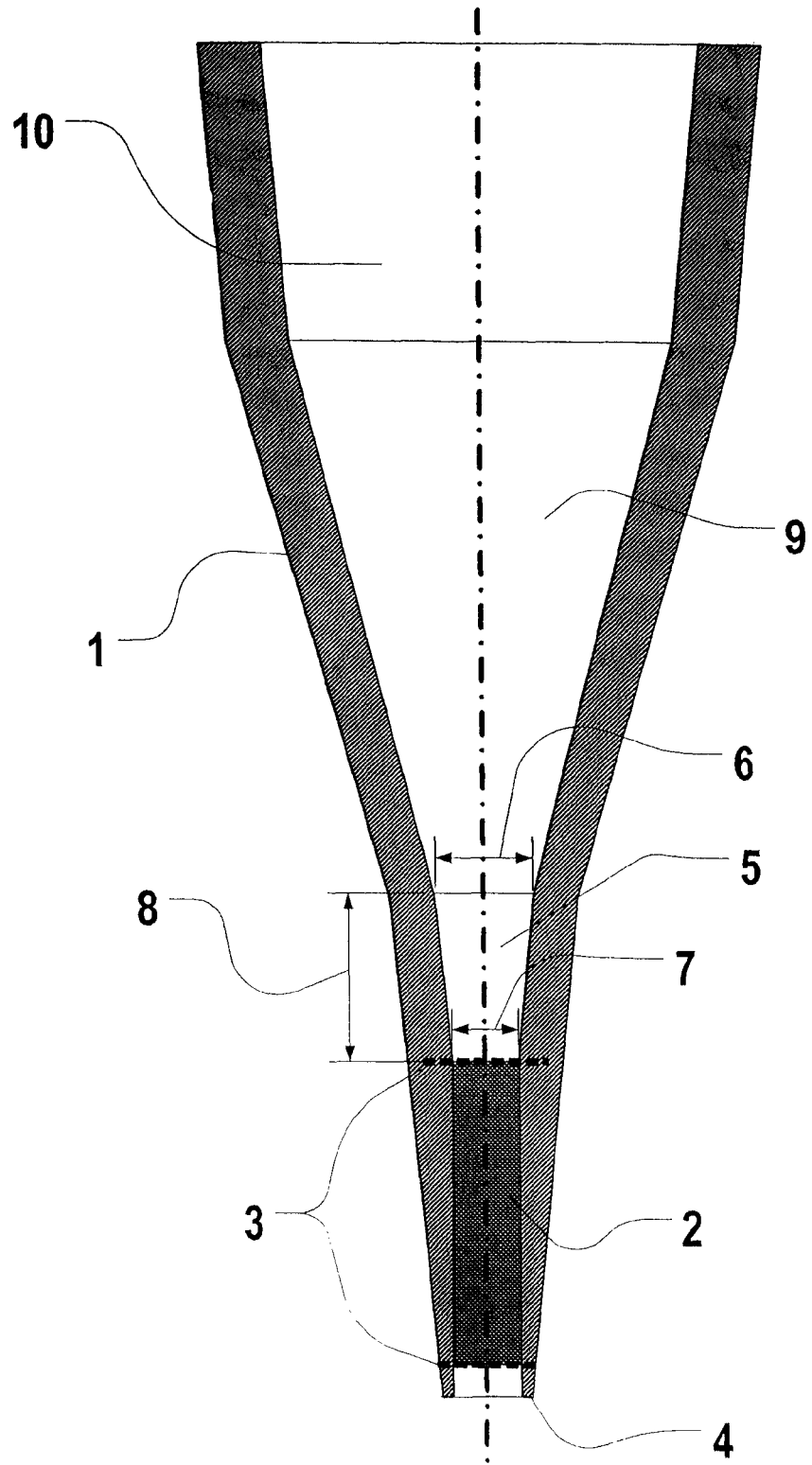
FIG. 1 is a cross-sectional view though a flow-through immunoassay unit constructed according to an embodiment of the present invention.

This invention has four related aspects. One aspect relates to the physical design of the assay unit. A second aspect is the method of operation for the assay unit in an immunoassay, particularly taking into account the removal of entrapped air in order to provide reproducible results. A third aspect is the design of an aspiration pump for optimal use with the assay unit to perform the method. A final aspect is the selection of the assay unit packed bed geometry (diameter and length) and particle size for optimal operation of the design in the method. These aspects will be first introduced generally and then described in detail.

Separation Unit Design.

The assay unit includes a packed bed of adsorbent particles contained within a cylindrical or frustum-shaped chamber by inlet and outlet screens or filters. The inlet to the packed bed includes a series of three open frustum-shaped open chambers, forming a tapered "cup". The successive chambers permits the unit to accept input from devices in a variety of sizes.

The chamber immediately adjacent to the inlet screen of the packed bed forms an "inlet seal" area, designed to reversibly connect by simple insertion to standard 10 and 200 µl pipette tips, as well as several standard gauge hypodermic needles or similar tubes, reliably forming a tight, relatively high pressure seal. The next chamber out is a "sample cup" designed to contain small volumes of samples or reagent to be introduced into the packed bed. The outer chamber is designed to mate and seal with the distal end of a standard 200 µL pipette holder or similarly-dimensioned device.

The outlet of the assay unit is also frustum-shaped, with an outer profile similar to the distal end of a standard 200 µL pipette tip. The outlet screen of the packed bed is located very close to the outlet port. This shape enables liquids flowing out of the assay unit to be deposited as small droplets on precise spots, such as MALDI-MS target plates. This shape also enables the outlet of the assay unit to be easily connected by simple insertion into a port with the same profile as the "inlet seal" of the assay unit itself. The overall geometry of the assay unit also enables the outlet of one unit to connect to the inlet seal of a second unit, enabling liquids to be transferred efficiently from one unit to another.

Method of operating the assay unit

In general operation, the outlet of the assay unit is inserted into an inlet connected to a pumping system (preferably an aspiration pump) capable of aspirating liquids through the outlet at a controlled flow rate. Reagents, samples or washing solutions are measured and dispensed into the sample cup chamber of the assay unit using standard manual pipettes or automated liquid handling systems. The measured volume of liquid is then pulled through the bed using the aspiration pump. In addition, it is possible to insert the distal end of the pipette tip used to measure the liquid directly into the inlet seal of the assay unit and leave the pipette tip behind as a "reservoir". This mode of operation is useful either for very small volumes to prevent transfer losses, or for larger volumes to extend the volume of the sample cup.

After all of the liquids required for each of the assay steps are pumped through the packed bed in this manner, an analytical measurement or result may be obtained in either one of two different general methods. In the first method, bound enzyme is measured by pumping a solution of enzyme substrate through a controlled flow rate, and substrate is converted to enzyme product in the packed bed at a rate which is a function of both the substrate flow rate and the amount of enzyme bound to the bed. The resulting enzyme product (and therefore bound enzyme reagent) concentration may be determined by collecting the product solution from the outlet of the assay unit in a microplate well and using a standard optical plate reader. Alternatively, the product concentration may be measured by connecting the assay unit outlet to an optical detector comprising a flow cell optically coupled to an appropriate light source and detector to measure the optical absorbance, fluorescence or chemiluminescence of the liquid emerging from the assay unit. In the second method of measurement, bound molecules, which may be labeled with a fluorescent marker, are eluted from the packed bed by pumping a solution through the bed that detaches the bound molecules from the binding. As is well know in the art, this is often done by salt or acid based elution solutions. The output from the assay unit is then measured optically, by fluorescent sensing, to determine the amount of the labeled molecule that was bound in the packed bed.

An advantageous part of the method of operation is a technique to remove air that remains entrapped in the packed bed after each aliquot of liquid has been aspirated through the assay unit. If the entrapped air bubbles are not removed, the surface area of the bed is reduced by a variable amount and the liquid flow path through the bed is disrupted, causing random variation in the final assay results. The entrapped air may removed by flushing the packed bed at a high flow rate with water or a wash buffer solution, either by positive displacement pumping or aspiration through the inlet seal or the outlet seal. The outlet of the liquid-filled bed assay unit can be inserted into a connection port which is partially filled with liquid to make a connection without entrapping further air. The inlet seal of the assay unit is left filled with liquid so that when a new sample or reagent liquid aliquot is dispensed into the sample cup, the liquids "merge" without entrapment of air bubbles. When this technique is employed between assay steps, the reproducibility of the assay system is dramatically improved.

When used for micro-volume sample preparation, the method of operation is similar. For the final step, instead of pumping enzyme substrate through the assay unit, an eluent solution (such as acid or salt) is pumped through the packed bed and the eluate liquid is collected from the assay unit outlet onto a surface or into a collection tube. It is also possible to operate the system with two assay units connected together so that liquid emerging from the outlet of one unit is transferred directly into the inlet of the second unit. This mode of operation is useful for multi-step separations or coupling of reactions with enzymes immobilized on the packed bed to downstream separation steps.

Aspiration Pump Design

The assay unit is designed so that reagents and samples can be added to the sample cup using standard manual pipettes or robotic liquid handling devices, then are pulled or aspirated through the packed bed by a pump connected to the assay unit outlet. A number of different approaches for this pumping could be used, but a syringe or piston type pump provides a good combination of relative simplicity, excellent flow and volume precision and low cost. One problem encountered, however, is that any bubbles present in any tubing connecting the pump to the assay unit cause the loss of precise control of the flow rate. Valves are also problematic because of the very low flow rates involved and the possibility of bubble entrapment or slow leakage, especially at negative pressure.

To overcome this limitation, a piston-type pump for use in aspiration has been designed so that the outlet of the assay unit inserts directly into a frustum-shaped inlet port very closely connected to the inlet of the piston cylinder. The piston is designed so that there is very little dead volume between the assay unit and the piston when the piston is fully inserted, in order to minimize the possibility of entrapped air bubbles. Once the aliquot of liquid has been aspirated completely through the packed bed, the assay unit is lifted out of the aspiration pump inlet port and the cylinder is emptied by moving the piston upward. A suction port entering the side of the pump inlet port located above the sealing point between the inlet port and the assay unit outlet pulls the expelled liquid out into a waste reservoir held under vacuum. A second port entering the side of the pump inlet may also be used is used to introduce liquids for washing the pump inlet, cylinder, piston and assay unit tip between cycles.

Bed Geometry

Working with this apparatus and this method has revealed a "window" of the combination of adsorbent particle type and size and packed bed geometry (diameter and length) which results in optimal operation in immunoassay applications. The combination comprises non-porous particles with an average diameter in the range of 20 to 150 μm. The particles must have an appropriate surface chemistry for irreversible binding of active antibodies, antigens or other coating reagents. The bed diameter is in the range the outer diameter of the distal end of standard pipette tips (0.5 to 1.0 mm) in order to meet the design constraints for the inlet seal and outlet of the assay unit itself. The bed length is selected to give a total adsorbent particle surface area in the packed bed of 0.5 to 2 square cm. For particles with a diameter in the range of 20 to 150 μm this gives bed lengths from 1 to 50 mm.

These elements will now be described in detail.

In FIG. 1, reference numeral 1 is directed to the assay unit of the present invention. FIG. 1 depicts the general layout and key features of the assay unit or assay unit 1, comprising a very small volume packed bed of particles 2. The packed bed 2 is contained within a cylindrical or frusto-conical reaction chamber or bed having a defined inlet and outlet sealed by a pair of porous bed supports 3. These bed supports may consist of any of a wide range of woven or non-woven screens, filters or membranes made from polymer, metal or paper with an average pore size which will contain the adsorbent particles. The outlet 4 from the packed bed chamber is located close to the distal end of the assay unit 1, and the shape of the outside of the distal end is designed to be identical to the outside of the distal end of a standard 200 μl, pipette tip, with a final diameter of less than 1 mm.

The inlet of the packed bed chamber is shaped so as to have three distinct frustum-shaped surfaces forming seals to which various input devices can mate in fluid-tight fashion. The surfaces are formed in series, forming a tapered receptacle serving as a sample cup for input reagents. Closest to the inlet of the packed bed 2 is the smallest sealing surface 5, which is frusto-conical in shape and has an inlet diameter 6, an outlet diameter 7 and a length 8 carefully defined to enable standard small volume pipette tips and standard gauge hypodermic needles and tubing to connect in a fluid-tight seal by simple insertion. Above the sealing surface 5 is another frusto-conical chamber serving as a sample cup 9, which has a volume designed to hold typical required amounts of samples or reagents, typically ranging from 5 to 100 µL. The final sealing surface 10, adjacent to the proximal end of the assay unit 1 is another frusto-conical sealing surface sized to fit and seal on the distal end of a standard 200 µL laboratory pipette (i.e. is shaped identically to the proximal end of a standard 200 µL pipette tip).

The dimensions of the inlet seal 5 are critical for enabling the inlet of the packed bed 2 to be in fluid-tight connection to a variety of different standard fluid handling devices. The inlet diameter 6 is selected so that the distal end of a standard 200 µL pipette tip 11 will just fit into the upper portion of the inlet seal 5, as shown in FIG. 2. This inlet diameter 6 is at least 1 mm and preferably in the range of 1.2 to 1.5 mm. The outlet diameter 7 is selected so that the distal end of a standard 10 µA pipette tip 12 will fit and just be prevented from touching the inlet retention means 3, as shown in FIG. 3. This outlet diameter 7 is less than 0.8 mm and preferably in the range of 0.7 to 0.75 mm. The inlet seal length 8 determines the angle between the walls of the inlet seal 5. This angle must be slightly greater than the outer angle of the standard pipette tips 11 or 12 in order to form a reliable seal on the very end of the tips to prevent dead spaces and holdup of liquids between the tip 11 or 12 and the inlet sealing surface 5. For commercially available tips, the angle between the center axis and the wall of the inlet seal 5 should be in the range of 5 to 7 degrees. With these dimensions, the inlet seal 5 will also seal as shown in FIG. 4 to standard straight wall tubing 13 between 0.75 and 1 mm OD, including 19 to 21 gauge hypodermic needles.

This type of sealing mechanism is highly reliable, with gentle force along the axis of the assay unit 1 being all that is required to make or break the seal. Seals can be easily be made by automated robotic systems, which aids in automating the entire assay process. Because of the very small diameters involved, the seals are capable of pressures in excess of 5 bar, even with just the friction of the interfering taper fit.

The uppermost hub 10 or chamber of the assay unit 1 enables the device to be placed on the end of a standard 200 µL laboratory pipette holder 14 or any other device with an identical profile, as shown in FIG. 5. In this mode, the assay unit 1 could be operated like other pipette tip-like solid phase extraction devices using air displacement to pull liquids in or push them out. However, it has been found that this means of operation is not as useful for the highly controlled application of samples and reagents required for precise assays. In the system of the present invention, the hub 10 feature is primarily used to enable a disposable pipette tip head on a robotic liquid handling system to pick up an assay unit 1 and place it in the proper location. Once in position, the normal tip ejection mechanism is used to release the unit 1 from the robotic head.

One important objective of the present invention is to functionally separate the steps of measuring and dispensing aliquots of samples, reagents, wash solutions and other liquids into the assay unit 1 from the step of pumping the liquid aliquots through the packed bed 2. This functional separation confers a number of significant advantages. Most conventional manual or automated liquid handling systems are capable of measuring and depositing a precise and accurate volume into a given location, but are not generally capable of providing tightly controlled flow rates because they operate using air displacement or air segmentation. However, any of these systems can be used for the measurement/loading step, imparting a great deal of flexibility to the design and operation of the required instrumentation, as well as making automation easier using standard components. In addition, a simple and inexpensive single channel liquid handling system can be used for measurement and dispensing in combination with a multi-channel flow system to obtain high assay throughput.

Figure 6:
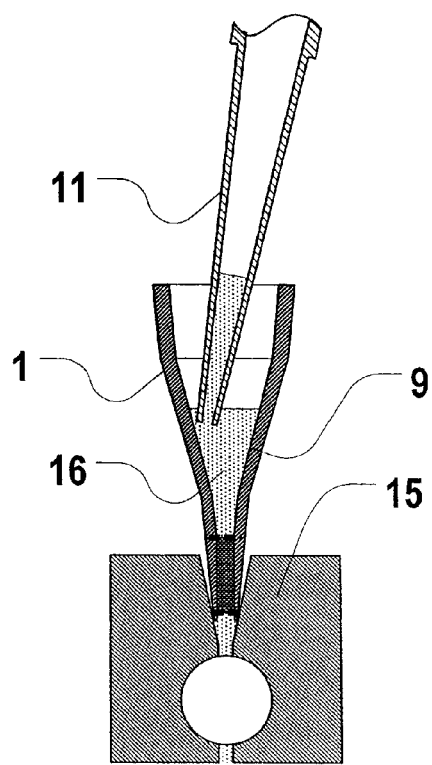
FIG. 6 is a cross-sectional view of the assay unit of FIG. 1 with one of the sealing surface areas being used as a sample cup.
Figure 7:
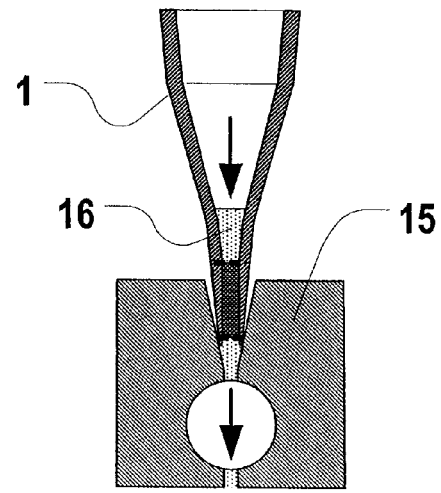
FIG. 7 is a cross-sectional view of the assay unit of FIG. 1 inserted into a aspiration pump in action.

This mode of operation is illustrated in FIGS. 6 and 7. The outlet of the assay unit 1 is inserted into an aspiration pump 15. This aspiration pump can be any pumping system capable of pulling liquids out of the assay unit 1 at a controlled and reproducible flow rate, independent of the flow resistance. Types of aspiration pumps could include positive displacement pumps such as piston or syringe pumps, peristaltic pumps or gear pumps. The aspiration pump 15 might also be a vacuum source connected to the assay unit 1 through a rapid acting solenoid valve or control valve to regulate the flow. The inlet port of the aspiration pump 15 is shaped similarly with dimensions similar to the inlet seal 5 of the assay unit 1 itself. The aspiration pump 15 can have a single pumping channel or have multiple pumping channels for operating several assay units 1 in parallel, either at the same flow rate or at different flow rates. A multi-channel aspiration pump 15 is advantageous for increasing the assay throughput of the system.

As shown in FIG. 6, an aliquot of sample or reagent liquid 16 is dispensed into sample cup 9 of the assay unit 1 with the aspiration pump 15 turned off. As shown in FIG. 7, the aspiration pump 15 is then turned on and the liquid aliquot 16 is pulled through the assay unit 1 at a controlled flow rate. Generally, in order to insure that the complete measured volume goes through the assay unit 1, the liquid is pulled through completely, which then pulls air into the packed bed 2. For an immunoassay, a series of reagents, samples and wash solutions are put through the assay unit 1 in the proper sequence using this mechanism.

Figure 8:
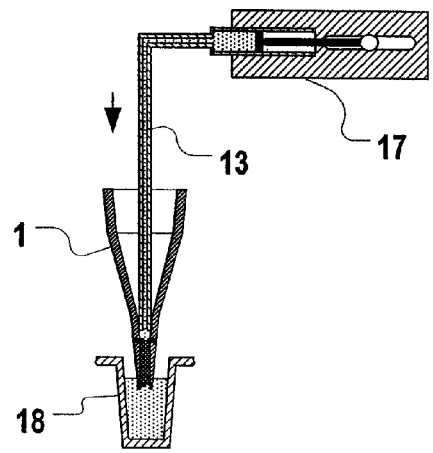
FIG. 8 is a schematic view showing the assay unit of FIG. 1 connected to a substrate pump for its input with its output emptying into a microplate well.
Figure 9:
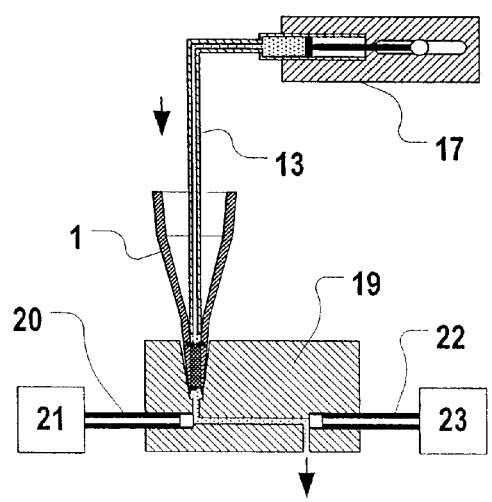
FIG. 9 is a view similar to FIG. 8 with an optical detection on the output of the assay unit based on absorbance.
Figure 10:
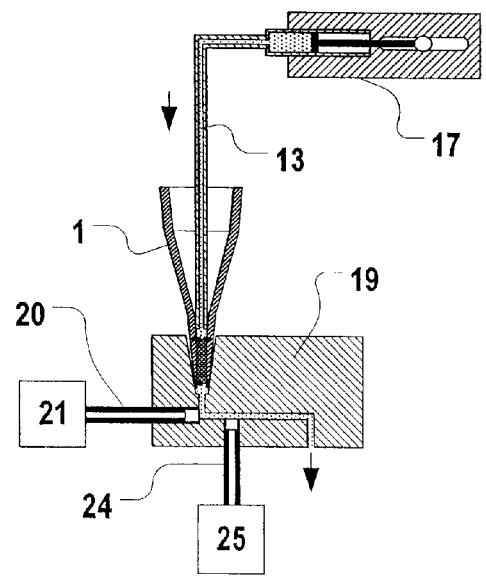
FIG. 10 is a view similar to FIG. 8 with an optical detection on the output of the assay unit based on fluorescence.

The final reagent is typically an antibody or antigen conjugated to an enzyme, which serves as the label for measurement. Detection and measurement of the level of enzyme conjugate bound to the assay unit 1 at the end of the assay steps is done by transferring the unit to a detection station, as shown in FIGS. 8 to 10. The inlet seal 5 of the assay unit 1 is connected via tubing 13 to a pump 17 which is filled with a solution of substrate for the enzyme. The substrate pump 17 may be any type of high precision positive displacement pump, including a piston or syringe pump, peristaltic pump or gear pump. Because the optical signal depends critically upon the substrate flow rate, precision, stability and lack of pulsation are critical characteristics of the substrate pump 17. In general, piston-type pumps give the best performance.

One mode of detection, shown in FIG. 8, is to collect the reacted product from the outlet of the assay unit 1 into the well 18 of a conventional microplate. Multiple assay units can be run and collected this way in parallel using a multi-channel substrate pump. Once a known volume of product solution is collected in the well, the microplate may be read in a conventional optical plate reader instrument, in order to determine the optical absorbance, fluorescence or chemiluminescence. This method has the advantage of utilizing widely available plate reader instrumentation.

A second mode of detection is to insert the outlet of the assay unit 1 into the inlet port of an optical flow cell 19 set up to read either the absorbance (FIG. 9) or fluorescence (FIG. 10) of the liquid entering the cell. A transparent illumination window 20, optionally with an optical fiber, is used to connect the flow cell to an appropriate light source 21, which may be monochromatic or polychromatic. For optical absorbance measurements, a second measurement window 22 is placed at the other end of the illuminated flow path facing the illumination window 20. The measurement window 22 is connected optically (optionally by a fiber) to an optical detector 23, which may be a simple photodetector if a monochromatic light source is used, or a spectrometer if a polychromatic light source is used. The detector 23 is used to measure the absorbance of the liquid in the flow cell at a particular wavelength. In an alternative configuration (FIG. 10), the measurement window 24 is placed at right angles to the beam from the illumination window 20 and is connected optically to an optical detector 25. This configuration is used for fluorescence measurements. If the light source is turned off, either configuration may be used for chemiluminescence measurements. The use of a flow cell has the advantages that a much smaller volume may be read, decreasing the readout time, and dynamic changes in the output as a function of operating conditions may be observed.

Figure 11:
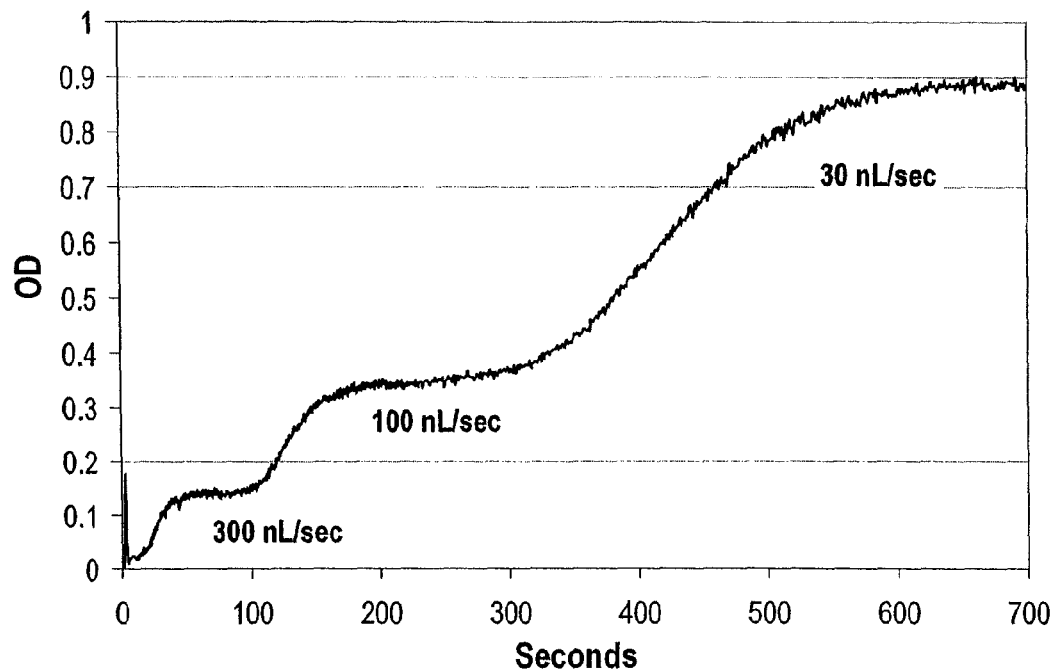
FIG. 11 is a graphical representation of some data obtained using the assay unit of the present invention, this data showing typical enzyme absorbance signal resulting from substrate being pumped through an assay unit containing bound enzyme conjugate at varying flow rates.

FIG. 11 shows a typical absorbance output from a system similar to that shown in FIG. 9. In this example, the packed bed contained 20 μm diameter non porous particles of polystyrene-divinylbenzene. The bed dimensions were 0.8 mm diameter and 5.5 mm long (3 μL bed volume). The assay unit was pumped with the following reagents in sequence:

| Volume | Reagent | Flow Rate |
|---|---|---|
| 10 μL | Coating antigen - 500 μg/mL bovine IgG (Sigma) in 50 mM carbonate pH 9.6 | 6 μL/min |
| 10 μL | Blocker - 10 mg/mL fish gelatin protein (Sigma) in 50 mM Tris, 0.14 M NaCl, 0.05% Tween 20 pH 8.0 | 24 μL/min |
| 10 μL | Conjugate sample -sheep anti-bovine IgG conjugated to horseradish peroxidase (Bethyl Labs) diluted to various concentrations in Blocker | 3 μL/min |
| 20 μL | Wash - 50 mM Tris, 0.14 M NaCl, 0.05% Tween 20 pH 8.0 | 500 μL/min |

This is an example of a "direct ELISA" assay, in which the solid phase is coated with antigen, non-specific adsorption sites are blocked and a sample containing a particular concentration of antibody-enzyme conjugate is applied.

Following the binding reactions, the assay unit was transferred to an absorbance detector system similar to that shown in FIG. 9 and pumped with a substrate solution (0.4 mM tetramethyl benzidine (TMB, Sigma) with 0.15% v/v hydrogen peroxide in 50 mM phosphate-citrate pH 5.0). The absorbance was measured at 650 nm. Note that normally the enzyme reaction in an ELISA must be "stopped" after a fixed time, usually with acid, in order to obtain a fixed reading. Since the assay unit 1 of the current invention is a flow-through system, the substrate stops reacting as soon as it leaves the packed bed 2, and no separate stopping step is necessary.

FIG. 11 shows the typical output signal. When substrate pumping begins, a short transient is experienced due to the refractive index difference between the final wash solution and the substrate solution. The signal then increases until it reaches a steady state at a particular flow rate. The time required to reach steady state will depend upon the liquid volumes in the assay unit 1 and the flow cell 18 as well as the substrate flow rate. The difference in optical density (OD) between the baseline and the steady state is the readout used to determine the sample concentration.

Figure 12:
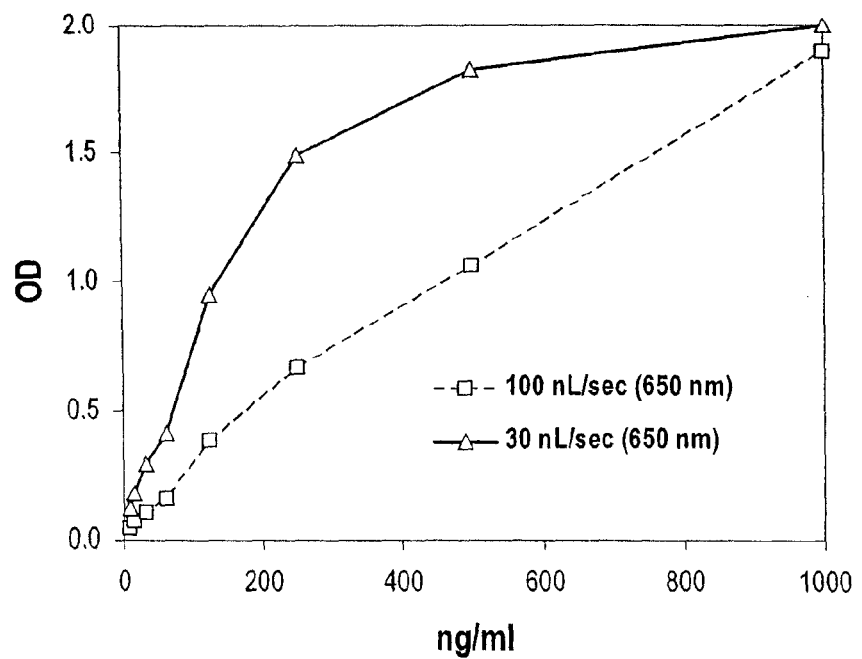
FIG. 12 is a graphical representation of data showing absorbance (OD) signals at two substrate flow rates as a function of sample concentration for direct ELISA assays run using the assay unit.
Figure 13:
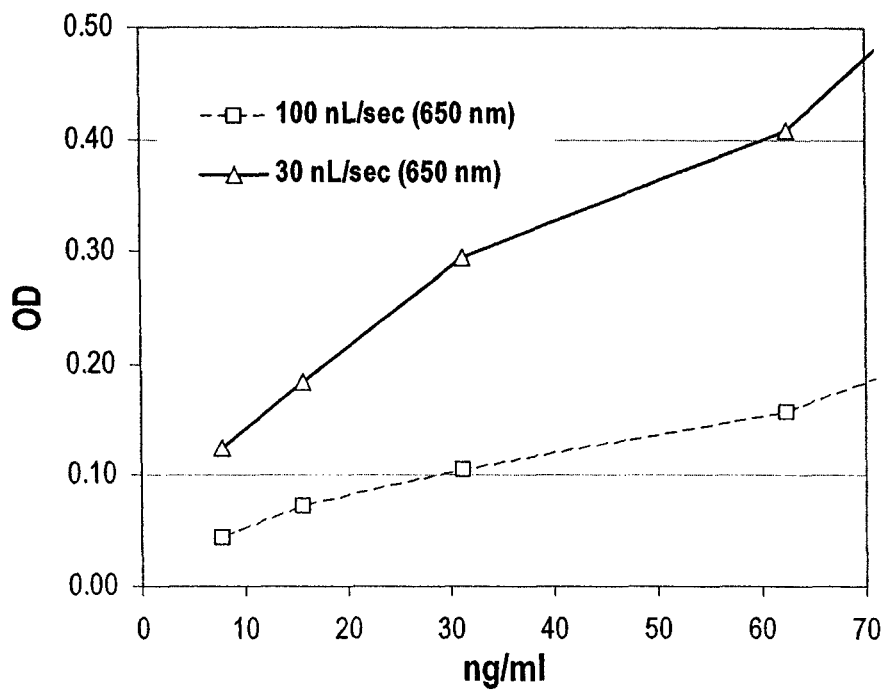
FIG. 13 is a graphical representation similar to FIG. 12 with reduced concentrations.

It may be observed in FIG. 11 that the signal increases as the substrate flow rate decreases. This feature enables the analytical sensitivity of the system to be adjusted by changing the substrate flow rate. Indeed, multiple flow rates may be run for each assay on the same sample, enabling multiple standard curves to be developed and a broader assay range to be covered. FIGS. 12 and 13 show plots at two different scales of the steady state OD signals at two different substrate flow rates over a range of different conjugate concentrations in the sample using the same assay protocol presented for FIG. 11. Each sample was measured at the two flow rates, producing two different curves. At 30 mL/sec substrate flow the assay is considerably more sensitive to lower concentrations (FIG. 13), but because bot the reaction and the detector can saturate, the assay becomes nonlinear above around 200 ng/mL conjugate (FIG. 12). However, the signal at 100 mL/sec substrate flow is linear up to 1000 ng/mL, providing an extended linear range for the assay.

Figure 14:
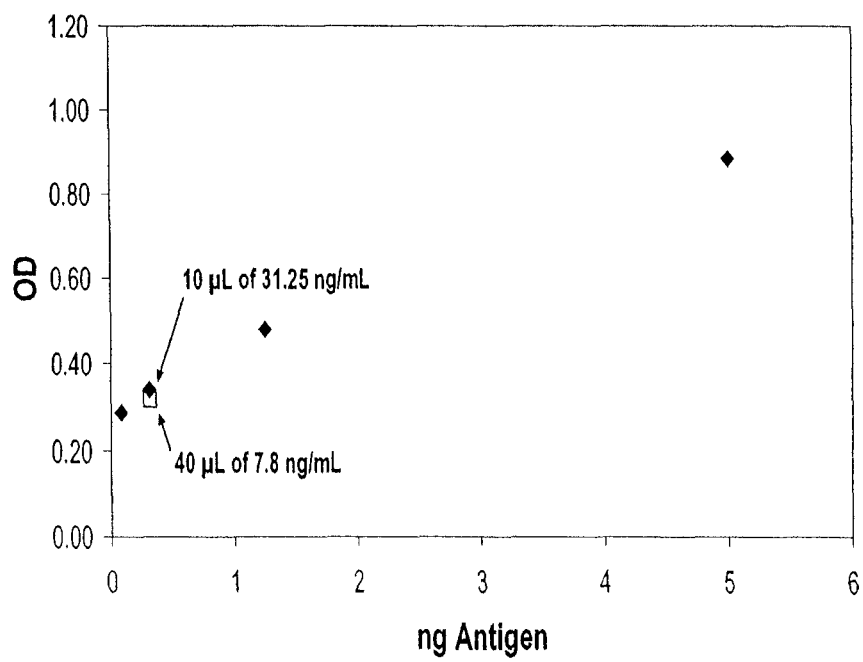
FIG. 14 is a graphical representation showing the absorbance (OD) signals at 30 nL/sec substrate flow rate as a function of sample mass for sandwich ELISA assays run in the separation unit.

FIG. 14 shows results using the system for a "sandwich" format ELISA using the system of the present invention. In this example, the packed bed contained 20 μm diameter non porous particles of polystyrene-divinylbenzene. The bed dimensions were 0.8 mm diameter and 5.5 mm long (3 μL bed volume). The assay unit was pumped with the following reagents in sequence:

| Volume | Reagent | Flow Rate |
|---|---|---|
| 25 μL | Coating antibody - 100 μg/mL sheep anti-bovine IgG (Bethyl Labs) in 50 mM carbonate pH 9.7 | 6 μL/min |
| 10 μL | Blocker - 10 mg/mL fish gelatin protein (Sigma) in 50 mM Tris, 0.14 M NaCl, 0.05% Tween 20 pH 8.0 | 24 μL/min |
| 10 μL | Antigen samples - Dilution of reference bovine serum with 28 mg/mL bovine IgG in Blocker | 3 μL/min |
| 10 μL | Conjugate - 5 μg/mL sheep anti-bovine IgG conjugated to horseradish peroxidase (Bethyl Labs) in Blocker | 3 μL/min |
| 30 μL | Wash - 50 mM Tris, 0.14 M NaCl, 0.05% Tween 20 pH 8.0 | 500 μL/min |

The assay units were run in the same system used for FIGS. 11-13, with the same enzyme substrate solution. The total time for all of the assay steps required was 11.2 minutes. The data showed good linearity over the range tested ($R^2=0.993$).

Note that FIG. 14 is plotted as OD signal vs. mass of antigen rather than the conventional concentration to illustrate an important feature of the assay method of the present invention. Because the solid phase is a flow-through packed bed as opposed to a standard microplate well, a very wide range of different sample volumes may be used. The volume in a microplate well is limited to a very small range (typically 50 to 100 μl, for a 96-well plate) in order to expose the sample to the entire coated binding surface. In the assay unit of the present invention, the binding surface is compressed into a small packed bed with a very small liquid volume (typically 0.5 to 2 μL). Target molecules in the sample bind to the bed as they flow through, and thus the bed serves as a "concentrator" for the sample. The two sample results highlighted in FIG. 14 had the same mass of target antigen (0.3125 ng), differing in volume and concentration (10 μL, of 31.25 ng/mL vs. 40 μL of 7.8 ng/mL), yet giving the same signal.

Reproducibility or precision is a critical element of any analytical method. Conventional microplate-based ELISA methods suffer from poor reproducibility (C.V.'s of 10 to 30% are typical) for a number of reasons. One is that it is difficult to precisely control the timing of the reagent or sample addition into all of the wells on the plate so that the incubation times for all of individual samples in the set are precisely the same for each well. Pipetting technique can also be critical and difficult to control reproducibly. During the incubation steps mixing from jarring, moving or vibrating the plates can cause variable results, as can temperature changes in the incubation environment. Even varying conditions between the outer and inner wells of a plate can give rise to variability in the final results.

The assay system of the present invention can substantially reduce or eliminate these sources of variability. Reagent addition (done at a controlled flow rate instead of by incubation) can be very reproducible with proper design of the pumps used. The issue of variable mixing is also dealt with by the use of flow through a packed bed. The most critical parameters controlling reproducibility are the measurement of the sample volume (all other reagents are added in excess, so volume control for them is less critical) and the flow rate of the substrate addition. These can be easily controlled to a precision of well under 5% using standard instrumentation.

One unexpected potential source of assay variability in the present invention proved to be the entrapment of air bubbles in the bed. One consequence of the use of an aspiration pump 15 in order to functionally separate the volume measurement and dispensing from the flow loading of an aliquot through the assay unit 1 (as illustrated in FIGS. 6 and 7) is that in order to deliver the entire aliquot of liquid 16 into the packed bed 2, it is necessary to pull air into the bed after each aliquot. It has been discovered that if the next aliquot of liquid is simply added, in the manner shown in FIG. 6, air bubbles of random volume and position may remain behind in the bed. These entrapped bubbles effectively block part of the bed from exposure to the liquid, and also disrupt the flow pattern within the bed, which can cause significant variability in the final assay results.

A solution to this problem is illustrated in FIGS. 15 and 16. A tube 13 connects the inlet seal 5 of the assay unit 1 to a syringe or pump filled with a wash solution. The wash solution is pumped through the packed bed 2 at a flow rate and volume high enough to dislodge and remove entrapped air through the outlet 4. It is also possible to remove air bubbles by filling the sample cup 9 with wash buffer and rapidly aspirating the liquid through the packed bed via a pump or syringe connected to the outlet 4.

The flow rate required for complete removal of entrapped air bubbles from the packed bed depends upon the diameter and length of the bed and the particle diameter. Generally, higher flow rates are required for larger beds and larger particle diameters. Testing with a 0.75 mm diameter, 3 µL bed of non-porous polystyrene-divinylbenzene beads indicated that volumes of 20 to 50 µL, were adequate for all bead diameters. The flow rate required for complete clearance of bubbles was at least 15 µL/sec for 20 µM diameter particles, 25 µL/sec for 50 µm diameter particles and greater than 50 µL/sec for 120 µm diameter particles. A simple way to provide these high flow rates is to connect the assay unit inlet seal 5 or outlet 4 to a spring, air or solenoid-actuated syringe that can provide substantial pressure to the liquid during the flushing step.

Once air removal is completed, the inlet seal 5 is left full of liquid 26 so that additional liquid added to the sample cup 9 will "merge" without entrapping a bubble. The liquid-filled assay unit may also be inserted into inlet ports 27 on the aspiration pump or flow cell without entrapping bubbles by having the port partially filled with liquid so that an initial "liquid seal" is formed before the solid seal is completed by insertion of the assay unit outlet 4.

FIG. 17 illustrates the effect of this air removal procedure on the assay reproducibility. In these experiments the packed bed contained 20 µm diameter non porous particles of polystyrene-divinylbenzene. The bed dimensions were 0.8 mm diameter and 5.5 mm long (3 µL bed volume). The assay unit was pumped with the following reagents in sequence:

| Volume | Reagent | Flow Rate |
|---|---|---|
| 10 µL | Coating antigen - 500 µg/mL bovine IgG (Sigma) in 50 mM carbonate pH 9.6 | 6 µL/min |
| 10 µL | Blocker - 10 mg/mL fish gelatin protein (Sigma) in 50 mM Tris, 0.14 M NaCl, 0.05% Tween 20 pH 8.0 | 24 µL/min |
| 10 µL | Conjugate sample - 250 ng/mL sheep anti-bovine IgG conjugated to horseradish peroxidase (Bethyl Labs) in Blocker | 3 µL/min |
| 20 µL | Wash - 50 mM Tris, 0.14 M NaCl, 0.05% Tween 20 pH 8.0 | varied |

The assay units were run in the system illustrated in FIGS. 11 to 13, with the same enzyme substrate solution. In the samples run without air removal, the assay steps were run as shown in sequence, and the final wash step was run at 24 µL/min. In the samples run with air removal, the assay unit was flushed after each step with 20 µL of wash buffer at 8 µL/sec (480 µL/min), and the final wash step was run at this same high flow rate. Each procedure was repeated with 5 identical samples. FIG. 17 shows the results from these examples. Without air removal, the coefficient of variation (C.V.) for the 5 runs was 22%, while with air removal the C.V. was 2%, thus demonstrating the dramatic improvement in reproducibility achieved by avoiding air entrapment.

An additional potential problem is with the aspiration pump 15 itself. Air bubbles present downstream of the packed bed 2 can cause variations in the flow rate. Since the major flow resistance is from the packed bed 2, the pressure downstream must be lower than atmospheric to cause flow, and bubbles trapped downstream will therefore expand in order to equalize the pressure. This can be a particular problem when the air-liquid interface passes through porous "barriers" created by the bed support 3 and the packed bed 2 as surface tension forces cause an increased pressure drop required for the interface to move through the barrier. Once the air passes through the barrier, the required pressure drop for flow decreases again. If bubbles are present downstream, they must then expand to enable flow to pass through the barrier (causing flow to temporarily slow or stop), then will contract once the barrier is passed (causing flow to suddenly increase until the bubble re-equilibrates). For this reason, it is critical to keep bubbles out of the liquid volumes downstream of the packed bed 2 as well.

Although a number of different types of pumps may be used for aspiration as described above, it has been found that a piston-type pump of the design shown in FIGS. 18 and 19 has a number of very important advantages. In this pump, a piston cylinder body 28 is inserted, or is formed integrally, into a pump block 29 which houses a reciprocating piston 30. The pump block 29 also has formed in it a frustro-conical shaped inlet port 31, larger at its upper end, which designed to seal with the outlet tip 4 of an assay unit 1, and open at its smaller lower end connecting into the interior of the cylinder body 28. The inlet port 31 opens into an inverted frustum shaped passage designed to fit tightly with the top of the piston 30. In addition, the inlet port 31 has a small lower side port 32 which connects the upper frustum to a small plenum 33. Optionally, the pump may also include a second upper side port 34 located above the lower side port 32 connecting the upper frustum to a second small plenum 35. As shown in FIG. 19, when the assay unit 1 is fully inserted into the inlet port 31 and the piston 30 is fully inserted, the sealing point 36 is located between the side port 32 and the top of the piston 30, thus closing off the fluid connection between them and permitting only a minimal liquid volume for possible bubble entrapment. In effect, the sealing point of the assay unit 1 itself serves as a valve, directing flow caused by the piston movement either through the packed bed or to the side ports 32 and 34 of the pump.

Figure 20:
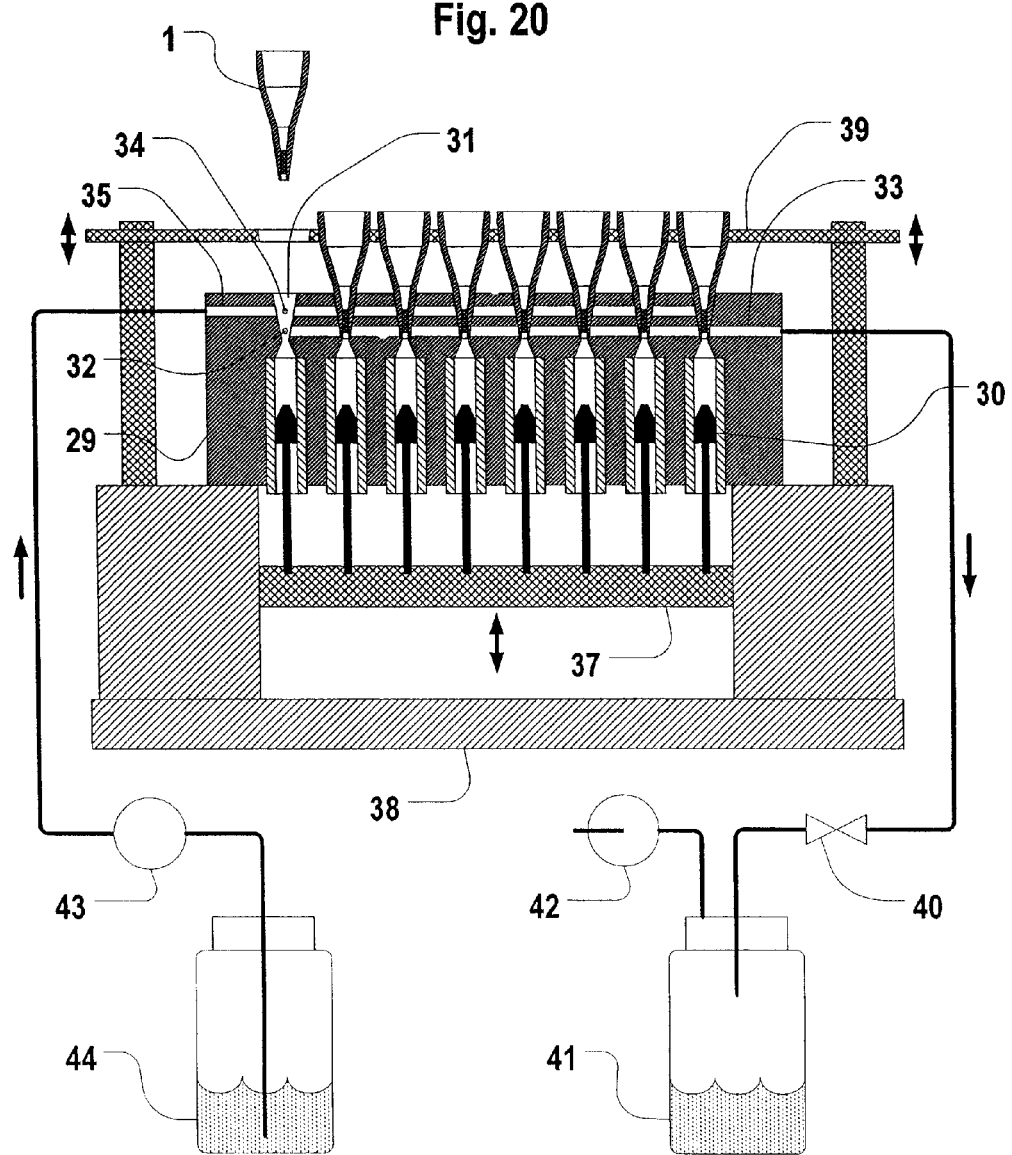
FIG. 20 is a cross-sectional view of a multi-channel pump system for use with an array of the assay units.

As shown in FIG. 20, it is possible to create a multi-channel array of a number of these pistons 30, inlet ports 31 and side ports 32 and 34 in combination, with the pistons 30 connected to a common drive mechanism plate 37, in turn connected to a drive mechanism 38 which moves all of the pistons up or down at the same time. In order to make the system compatible with common liquid handling devices, it is advantageous to arrange the cylinders and inlet ports in linear arrays with the ports on 9 mm centers. In addition to the single linear array shown in the figure, it is also possible to have a two-dimensional array, for example with 96 channels arranged in 8 rows of 12, similar in layout to a standard 96-well microplate. The first side ports 32 are connected to a common plenum 33, which is in turn connected through a valve 40 to a closed collection reservoir 41 connected to a vacuum pump or source 42. When the valve 40 is opened, any liquid in the inlet ports 31 above the lower side ports 32 will be removed by suction through the plenum 33 into the collection reservoir 41.

Similarly the second side ports 34 are connected to a second plenum 35 which is in turn connected to a pump 43 and one or more reservoirs 44 of liquid used for washing out the inlet ports 31. When pump 43 is activated, wash liquid from reservoir 44 is pumped into all of the inlet ports 31 simultaneously. The system is also equipped with a locator plate 39 through which the assay units may be inserted and held without moving relative to the plate. The plate may be driven up or down by an actuator, causing all of the assay units 1 to be moved up or down at once relative to the aspiration pump block 29.

Figure 21:
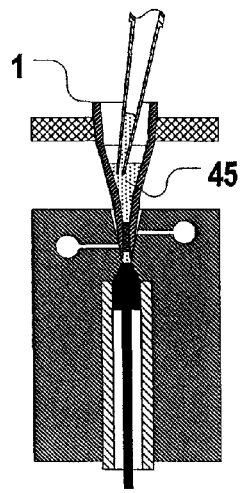
FIGS. 21 through 28 are cross-sectional views illustrating steps in the use of the pump and assay unit of the present invention.
Figure 22:
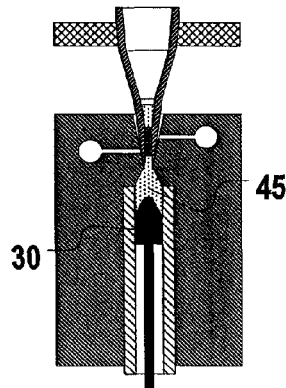
Figure 23:
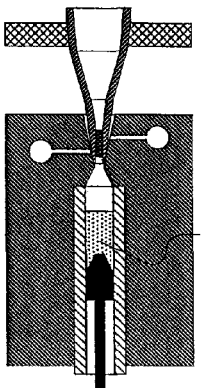
Figure 24:
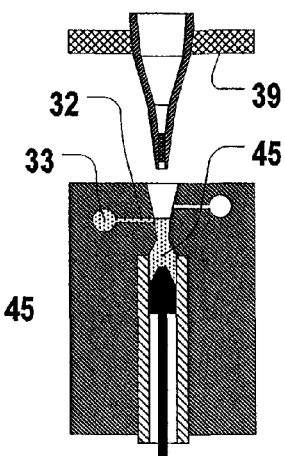

The operating cycle of this pump is shown in FIGS. 21 to 28. In FIG. 21, an assay unit 1 is inserted into the pump and a pipette or other liquid handling device is used to deposit a precisely measured volume of liquid 45 (reagent, buffer, sample, etc.) into the sample cup of the assay unit 1. To start the flow (FIG. 22), the piston 30 is moved downward at a controlled speed by the pump drive, which in turn pulls the liquid 45 through the assay unit 1 packed bed at a controlled flow rate. In order to insure that all of the liquid 45 is exposed to all of the packed bed for a controlled time, the piston 30 is pulled down far enough (FIG. 23) so that air is pulled through the assay unit 1 packed bed. The assay unit 1 is then moved upward (FIG. 24) by the locator plate 39 so that the seal with the inlet port is broken, making a fluid connection between the top of piston 30, the side port 32 and the plenum 33. The piston is then moved upward to the top of its stroke to expel the liquid 45 upward. Suction applied to the plenum 33 pulls the liquid out the side port 32 where it is carried away through the plenum 33 to a waste collection reservoir.

Figure 25:
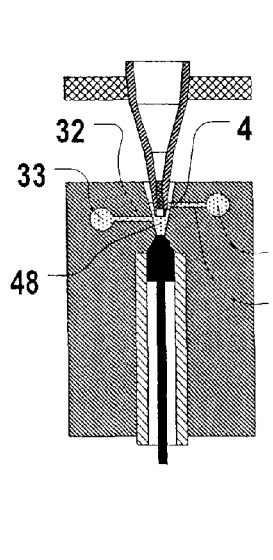
Figure 26:
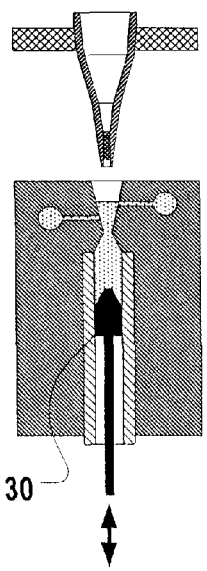

As shown in FIG. 25, the assay unit 1 may be moved downward until its outlet tip 4 is located between the first side port 34 and the second side port 32. In this position, wash liquid 48 may be pumped in through the upper plenum 35, through the upper side port 34 and sucked out through the lower side port 32 into the lower plenum 33. This flow of liquid can be used to wash out the inlet port 31 as well as the outside of the assay unit 1. As shown in FIG. 26, the assay unit can be withdrawn and the washing flow continued while the piston 30 is moved up and down in order to wash the piston and cylinder.

Figure 27:
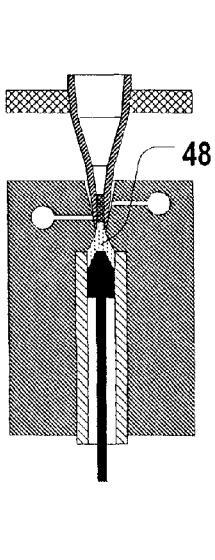
Figure 28:
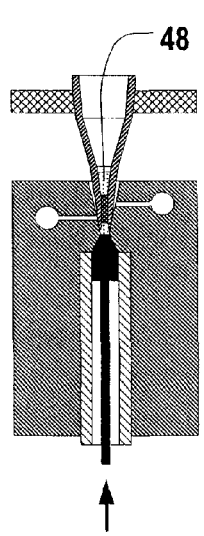

The small amount of wash liquid 48 remaining in the inlet port below the side port 32 is used to form a "liquid seal" (as illustrated in FIG. 16) when the assay unit 1 is reinserted to complete the cycle (FIG. 27). If a small amount of wash liquid is held in the cylinder by keeping the piston 30 partially withdrawn during this step, once the seal with the assay unit 1 is made, the piston 30 can be driven up quickly, expelling the air from the packed bed and leaving a small amount of wash liquid 48 in the inlet seal to start the next cycle.

The same assay unit of the present invention can also be used in a micro-preparative mode to purify particular molecules of interest for other micro-scale analytical techniques such as mass spectroscopy. In this mode, packed bed contains any of a number of different particulate adsorbents (including but not limited to porous or non-porous particles, made of materials such as polystyrene-divinylbenzene, polyacrylamide, agarose, cellulose, silica, alumina, zirconia, composites thereof and the like) with immobilized binding molecules (including but not limited to antibodies, antigens, nucleic acids, hormones, cytokines, receptors, enzymes, and the like) or other selective surface chemistries (including but not limited to ion exchange, reversed phase, hydrophobic interaction, gel filtration, affinity chromatography, mimetic ligand chromatography, metal chelate chromatography and the like). Samples containing the target molecules are passed through the packed bed and bind to the selective adsorbent particles and non-binding contaminants are washed away. Then the bound target is eluted using, for example, acid or a salt solution, for collection into a tube or on a surface spot for further analytical processing. It is also possible to immobilize an enzyme (including but not limited to proteases, kinases or glycosidases) to the packed bed to enable very rapid selective digestion or other processing of the target molecule as it passes through the packed bed at a controlled flow rate prior to further analysis.

Figure 29:
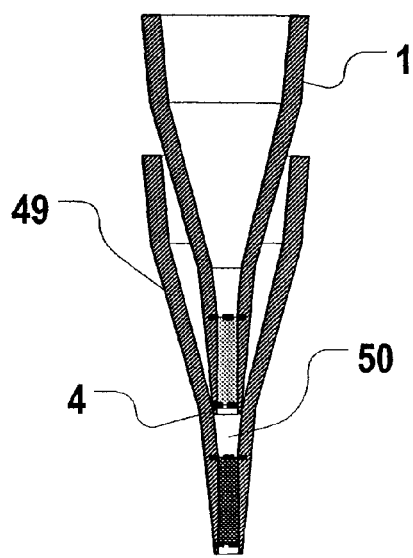
FIG. 29 is a cross-sectional illustration of two nested assay units.

Two additional modes of operation are useful for these micro-preparative separations. FIG. 29 shows two assay units (1 and 49) connected together by the outlet 4 of the first assay unit 1 inserted into the inlet seal 50 of the second assay unit 49. This mode of operation is useful for several applications. One would be to combine multiple separation steps on an automated system. For example, the first assay unit 1 could contain an ion exchange packing to selectively bind and purify the target from a complex sample such as blood serum or cell culture supernatant. Elution from this packing is through the use of a high concentration of salt, which is not compatible with mass spectrometry. If the second assay unit 49 contains a reversed-phase packing, when the target is eluted from the first assay unit 1 into the second assay unit 49 it will be bound on the reversed phase packing. After the assay units 1 and 49 are decoupled the salt can be washed away, and the target eluted from the second assay unit 49 using an organic solvent solution that is compatible with the mass spectrometer.

A second type of application for the mode of operation illustrated in FIG. 29 is the use of an immobilized protease, such as trypsin, in the first unit 1. During passage of a sample aliquot through the first unit 1, the proteins present would be digested by the immobilized enzyme into defined peptides. By using immobilized enzyme, a much higher amount of enzyme can be used than is normally employed in the solution phase, giving rise to a faster digestion with no chance of autolysis products from the enzyme contaminating the analysis. If a reversed phase packing is used in the second unit 49, the digested peptides would be captured and concentrated, and any salt required in the digestion buffer would be removed by washing after the assay units 1 and 49 are decoupled. The peptides could then be eluted in an organic solvent solution that is compatible with the mass spectrometer.

Figure 30:
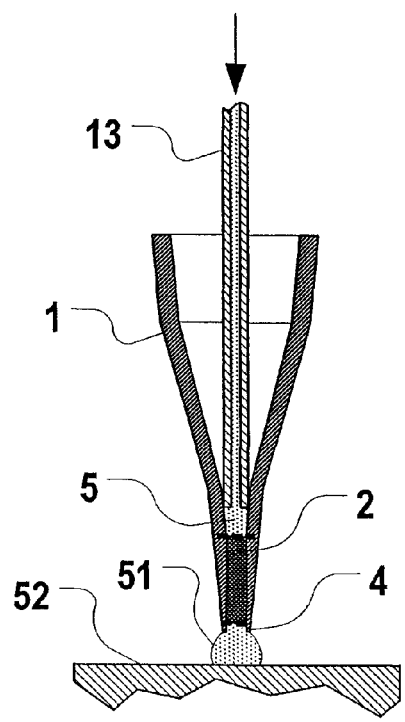
FIG. 30 shows a cross-sectional view of an assay unit with a needle inserted pumping eluent through the bed of the assay unit.

FIG. 30 illustrates the preferred mode of elution from the assay unit 1 for micro-preparative applications. Eluent solution is pumped through a tube 13 connected to the inlet seal 5 of the assay unit 1. After passing through the packed bed 2, the eluate 51 emerges from the outlet tip 4 as a small droplet. The eluate can be collected in very small volumes (less than 1 μL is possible) by gently touching the outlet tip 4 with the hanging droplet onto a surface 52, which may be a MALDI MS target plate, test tube, microplate well, electrophoresis gel well, etc. Alternatively, the outlet tip 4 could be inserted directly into the inlet port of an electrospray ionization mass spectrometer and the eluted product analyzed directly by pumping into the instrument at a controlled flow rate.

The design of the packed bed of the assay unit, including the diameter and length of the bed and the type and diameter of the adsorbent particles, is critical for optimal operation in the immunoassay application. With a standard microplate-type ELISA, each of the reagents and samples are incubated in the well for a set period of time in order to expose the molecules in the solution to the binding molecules coated on the surface of the wall of the well. Although all of the molecules in the well are available for binding, the only way they can reach the wall is through molecular diffusion, which is rather slow for large molecules such as proteins. Thus each step requires an incubation period ranging typically from half an hour to overnight or longer to reach the binding level desired. Often the time required to complete binding equilibrium is impractically long and therefore shorter times are used, preventing the binding reaction from going to completion. This causes the assay results to vary significantly depending upon the exact timing, temperature, and mixing events, such as jarring or moving the plate.

By contrast, in the assay unit of the present invention, the binding surface is provided by the packed bed of adsorbent particles. Molecules are exposed to the binding surface by flowing through the packed bed. Because the diffusion path for the molecules had been greatly reduced (to just the spaces between the particles and potentially pores within the particles), the time required to reach binding equilibrium is greatly reduced. This not only makes the assay much faster, but also significantly reduces or eliminates the common sources of assay variability.

However, although the mass transport in the packed bed is greatly improved, the rate of binding of molecules from the solution to the surface (or to capture) is not infinite. If the flow rate through the bed is too high, molecules will not have a chance to bind and will flow through the bed, resulting in incomplete capture. On the other hand, if the maximum flow rate for effective capture is too slow, the steps of the assay will take too long, reducing the some of the advantages of the system described here over conventional methods.

At least two factors determine the maximum flow rate for effectively complete capture—the mass transport from the liquid phase to the solid surface and the kinetics of the binding reaction itself. Mass transport to the binding surface, in turn, has two major components; transport from the bulk liquid to the surface of the adsorbent particles by a combination of convection and diffusion, and transport within the pores of the particles (if any) by diffusion. Many investigators have studied mass transport in this type of system in the context of chromatography (Kopaciewicz et al, *Journal of Chromatography*, 409:111 (1987)), and this work has shown that the diffusion within the pores is by far the slower of the two mass transport elements. This can be mitigated to some extent by using porous particles with some very large pores that allow convective flow through the particles. (Afeyan et al, *Journal of Chromatography*, 519:1 (1990)) However, intra-particle diffusion can be completely eliminated by using non-porous particles. (Kalghatgi and Horvath, *Journal of Chromatography*, 398:335 (1987)). Chromatographic applications require a relatively high binding surface area per unit volume in order to have useful capacity, so the non-porous particles used have typically been very small (1 to 3 μm). With particles this small, pressure drops at normal flow rates are very high, requiring special high pressure pumps and other equipment.

For the immunoassay application, however, the required surface area is actually quite low. A standard microplate well filled with the normal 50 to 100 μL of sample or reagent has a solid phase surface area of approximately 1 to 2 square cm. This corresponds to a total amount of antibody coated on the surface of around 400 to 800 ng. (Cantarero et al, *Analytical Biochemistry*, 105:375 (1980)) Any surface area larger than 1 to 2 square cm would result in excessive use of the expensive antibody or antigen reagents compared to a microplate assay. Because of this low surface area requirement, relatively large diameter non-porous particles can be used in a packed bed for immunoassays, eliminating the problems with high pressure drops, which is particularly important when pumping liquids through the packed bed.

In the apparatus described here, non-porous adsorbent particles can be used for immunoassays as the solid phase in the packed bed. The particles may be made of a variety of polymers (including but not limited to polystyrene-divinylbenzene, polyacrylamide, polyvinyl chloride and the like) or inorganic materials such as silica, alumina, zirconia or carbon. Antibodies or antigens may be coated on the surface by passive adsorption or by covalent coupling. The particles may also be coated with a hydrophilic polymer to prevent non-specific adsorption, on which covalently reactive groups are placed to enable covalent coupling of the coating molecules. Coupling may also be through specific non-covalent binding, such as the streptavidin-biotin system.

The diameter of the packed bed is limited by the physical design constraints of the assay unit, as described above. The inlet diameter of the bed must be approximately the same as the outlet diameter of a standard 10 μL pipette tip, or less than 0.8 mm. The outlet diameter of the bed must be less than the diameter of the assay unit itself at the outlet bed support (typically 1 to 1.2 mm) minus twice the wall thickness of the assay unit (typically 0.2 mm) or approximately 0.6 to 0.8 mm. In order to reduce problems with plugging of the bed and minimize the pressure drop, the bed diameter should be as large as possible.

In the present invention, once the packed bed diameter is set, the packed bed length is then determined by the combination of the bed diameter and the adsorbent particle diameter in order to give a total adsorbent surface area in the required range of 1 to 2 square cm. The surface area per unit volume for uniform spheres is given by the following equation:

$$a = 6(1-\epsilon)Dp$$

where a is the area per unit volume, ε is the void fraction of the bed (the part of the volume outside the particles) and Dp is the adsorbent particle diameter. The following table shows the bed dimensions and volumes as a function of particle size for beds with a diameter of 0.75 mm, a void fraction ε of 0.4 and a packing surface area of 2 cm, which are typical of the present invention:

| Particle Diameter Dp μm | Bed Length L mm | Bed Volume Vbed μL | Void Volume Vo μL |
|---|---|---|---|
| 10 | 1.2 | 0.6 | 0.2 |
| 20 | 2.4 | 1.1 | 0.4 |
| 30 | 3.7 | 1.7 | 0.7 |
| 40 | 4.9 | 2.2 | 0.9 |
| 50 | 6.1 | 2.8 | 1.1 |
| 75 | 9.1 | 4.2 | 1.7 |
| 100 | 12.2 | 5.6 | 2.2 |
| 150 | 18.3 | 8.3 | 3.3 |

The adsorbent particle diameter is selected in order to maximize the flow rate that can be used and still get effectively complete capture. As mentioned above, the capture rate may be limited either by mass transport to the surface or the kinetics of the binding reaction. The mass transport to the surface is expected to be influenced by the particle diameter, since the smaller the particles, the smaller the diffusion path in the spaces between the particles and the larger the surface area exposed per unit volume of liquid in the bed.

In order to demonstrate this effect, an experiment was performed using beds of 0.76 mm diameter and 5.1 mm in length packed with 4 different diameter ranges of cross-linked, non-porous polystyrene-divinylbenzene beads. A 10 μL sample of 25 ng/mL sheep anti-bovine IgG conjugated to horseradish peroxidase (Bethyl Labs) in 50 mM carbonate buffer pH 9.6 was passed through the packed bed at a desired flow rate, then washed immediately out with 200 μL of distilled water. After this, the amount of bound enzyme in the packed bed was measured with a substrate flow rate of 100 mL/sec as described in FIGS. 11 to 13.

Figure 31:
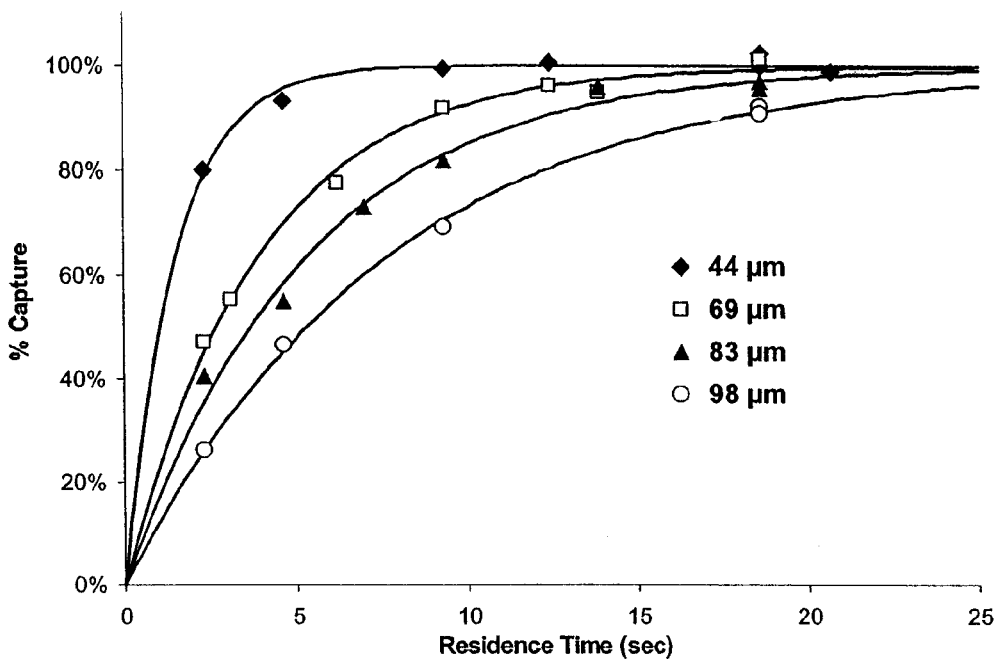
FIG. 31 shows the fraction of an antibody-enzyme conjugate captured in assay units as a function of the residence time in the unit for different particle diameters of the packing material.

In this experiment, the binding reaction is simply the hydrophobic adsorption of the antibody-enzyme conjugate to the surface of the beads. This reaction is expected to be mass transport limited rather than binding kinetics limited. FIG. 31 shows the results, plotted as the % capture versus the residence time (equal to the void volume of the column (1.02 μL) divided by the flow rate). As the residence increases (i.e. the flow rate decreases), the amount of capture approaches 100%. However, the residence time required for complete capture increased with the particle diameter as expected. Thus, looking only at the mass transport, smaller particle size would enable faster flow rates for complete capture.

However, the other potential factor determining the maximum flow rate for effective capture is the kinetic on-rate of the binding reaction itself. There is some variation in the on-rate, depending upon the size of the antigen and the location of the binding site. If the rate of binding is kinetically limited (rather than mass transport limited) the maximum flow rate for effective capture should depend only upon the packed bed volume and not on the bed geometry or particle diameter.

Experiments were conducted with different packed bed diameters, volumes and particle sizes to confirm these relationships. The reagents used and the sequence of operation were similar to those shown in FIGS. 11 to 13, with a conjugate sample concentration of 200 ng/mL and a substrate flow rate of 100 mL/sec. The loading flow rate for the conjugate sample step was varied, and the final OD was determined at each flow rate. Several different size columns packed with different amounts of different adsorbent particle diameters were used. The following table summarizes the results:

| | | | | 95% Capture | |
|---|---|---|---|---|---|
| Particle Diameter μm | Bed ID mm | Bead Weight mg | Void Volume μL | Flow Rate μL/min | Residence Time sec |
| 20 | 0.50 | 0.58 | 0.35 | 0.9 | 22 |
| 20 | 0.50 | 0.69 | 0.42 | 1.0 | 25 |
| 20 | 0.75 | 1.15 | 0.70 | 1.6 | 26 |
| 20 | 0.75 | 1.38 | 0.84 | 2.1 | 24 |
| 50 | 0.75 | 1.38 | 0.84 | 2.0 | 25 |

The data show that at least for this particular antibody-antigen binding reaction, a residence time (void volume divided by flow rate) of approximately 25 seconds is required for 95% capture, over a fairly broad range of bed dimensions and particle diameters. This is much greater than the residence times required for the binding reaction for these diameter particles shown in FIG. 31 (5 seconds or less). This suggests that the binding reaction on-rate is limiting in this system.

Figure 32:
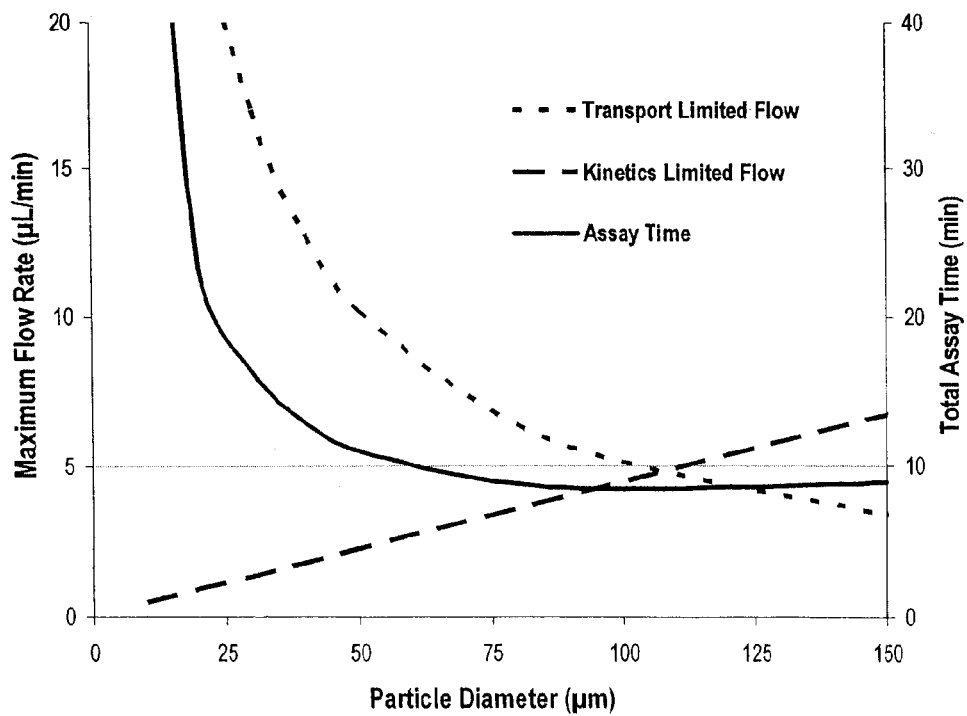
FIG. 32 shows calculations from an engineering design model based on the data in FIG. 31 for the maximum flow rate for 95% capture through an assay unit and the resulting assay time, as a function of the packing particle diameter.

FIG. 32 shows calculations from a mass transport and kinetic model based on these data. In the model, packed beds with a diameter of 0.75 mm and a binding surface area in the bed of 2 square cm are assumed, as shown in Table 4. The curve for "Transport Limited Flow" shows the maximum flow rate at which there is 95% capture of molecules by a rapid reaction, limited by mass transport, such as binding to the surface during coating or blocking steps of an assay. The maximum flow rate decreases with increasing particle diameter, as shown by the data in FIG. 31.

The curve for "Kinetics Limited Flow" shows the maximum flow rate at which there is 95% capture of molecules for a reaction with a higher required residence time (30 seconds in this case), such as the antigen-antibody binding reactions of the sample loading and second antibody conjugate loading steps of an assay. Somewhat surprisingly, the kinetics limited flow rate increases linearly with increasing particle size. This is because larger particle diameters require larger packed beds in order to keep the constant surface area. A larger bed can be operated at a higher flow rate for the same residence time than a smaller bed.

The curve for "Assay Time" shows the sum of these two effects, assuming 10 μL volumes for each of the four main steps in an assay—coating and blocking (transport limited) and sample and conjugate (kinetics limited). Below around 25 μm particle diameter the assay time increases sharply, reaching a minimum around 100 μm and increasing slowly for larger particle diameters. Mass transport effects dominate above about 100 μm particle diameter.

To summarize these considerations, the apparatus described here is optimally operated for immunoassay applications with a packed bed of non-porous particles, with a particular operating "window" of the combination of bed diameter, bed length and average particle diameter. The bed diameter is constrained by the design of the assay unit to a range of 0.5 to 1.0 mm, preferably in the range of 0.7 to 0.8 mm. The bed length is then determined by the required bed volume, which is in turn determined by the adsorbent particle diameter such that the total particle surface area in the bed is in the range of 0.5 to 2 square cm, preferably close to 2 square cm. The average particle diameter is determined by a combination of mass transport and kinetic considerations, and is in the range of 20 to 150 μm, most preferably in the range of 40 to 100 μm.

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

We claim:

1. An immunoassay or selective adsorption assembly comprising a flow-through assay unit and an aspiration pump; wherein the flow-through assay unit includes a pair of porous bed supports trapping between them solid phase support beads with a reaction reagent mounted on their surface, an open proximal end, and an open distal end of smaller diameter than the proximal end; wherein the aspiration pump includes a pump block, a piston, and an inlet port formed in the pump block and sized to receive the distal end; the aspiration pump is in fluid communication with the flow-through assay unit via the distal end to draw fluid therethrough; the aspiration pump is vertically oriented with the inlet port being conical at a top of the aspiration pump; and the assay unit has a corresponding tapered opening at the distal end so that the assay unit is mountable upon the pump in fluid-tight fashion.

2. An immunoassay or selective adsorption assembly as claimed in claim 1 wherein the flow-through assay unit also includes a plurality of sealing surfaces of frusto-conical shape and of differing sizes to accommodate fluid tight communication with a variety of fluid handling equipment.

* * * * *